(12) United States Patent
Sakagami et al.

(10) Patent No.: US 8,246,553 B2
(45) Date of Patent: Aug. 21, 2012

(54) MUSCLE HARDNESS METER

(75) Inventors: Toshimasa Sakagami, Tokyo (JP);
Hiroshi Karasuno, Koriyama (JP);
Hisashi Kuroda, Tokyo (JP); Makoto Sasaki, Tokyo (JP); Wataru Orito, Tokyo (JP)

(73) Assignee: Ito Co., Ltd., Tokyo (JP)

( * ) Notice: Subject to any disclaimer, the term of this patent is extended or adjusted under 35 U.S.C. 154(b) by 219 days.

(21) Appl. No.: 12/598,339

(22) PCT Filed: Aug. 23, 2007

(86) PCT No.: PCT/JP2007/066360
§ 371 (c)(1),
(2), (4) Date: Jan. 12, 2010

(87) PCT Pub. No.: WO2008/136140
PCT Pub. Date: Nov. 13, 2008

(65) Prior Publication Data
US 2011/0130682 A1 Jun. 2, 2011

(30) Foreign Application Priority Data
May 1, 2007 (JP) .............................. 2007-120861

(51) Int. Cl.
*A61B 19/00* (2006.01)
*A61B 5/00* (2006.01)
*A61B 5/103* (2006.01)
*A61B 5/117* (2006.01)
*G01N 3/48* (2006.01)
*G01N 3/42* (2006.01)

(52) U.S. Cl. ............ 600/587; 600/553; 600/561; 73/81; 73/82

(58) Field of Classification Search ...... 73/81; 600/500, 600/552–553, 557, 561, 587
See application file for complete search history.

(56) References Cited

U.S. PATENT DOCUMENTS
3,133,355 A * 5/1964 Gordon ......................... 600/587
(Continued)

FOREIGN PATENT DOCUMENTS
JP 10-085191 4/1998
(Continued)

OTHER PUBLICATIONS

Korean Office Action for corresponding KR10-2009-7022168 dated Feb. 14, 2011.
(Continued)

*Primary Examiner* — Sean Dougherty
(74) *Attorney, Agent, or Firm* — K&L Gates LLP

(57) ABSTRACT

A muscle hardness meter according to the present invention, which measures the hardness of muscle tissue of a living organism, includes: an auxiliary part which touches a periphery of a section of the living organism to be measure so as to apply pressure to the periphery; a touching part which touches the section to be measured so as to apply pressure to the section to be measured; a first pressure sensor which measures pressures that the touching part and the auxiliary part sustain, respectively, from the section to be measured and the periphery, and outputs a first measurement result; a second pressure sensor which measures a pressure that the touching part sustains from the section to be measure, and outputs a second measurement result; a notification part which notifies the second measurement result; and a control part which determines whether or not the first measurement result teaches a reference pressure value input in advance and notifies the second measurement result to the notification part at a time when it is determined that the first measurement result reaches the reference value.

6 Claims, 6 Drawing Sheets

U.S. PATENT DOCUMENTS

| | | | | |
|---|---|---|---|---|
| 4,159,640 | A * | 7/1979 | Leveque et al. | 73/81 |
| 4,269,193 | A * | 5/1981 | Eckerle | 600/485 |
| 5,224,469 | A * | 7/1993 | Mocny | 601/108 |
| 5,766,137 | A * | 6/1998 | Omata | 600/587 |
| 5,879,312 | A | 3/1999 | Imoto | |
| 5,911,694 | A * | 6/1999 | Ikeda et al. | 600/587 |
| 6,063,044 | A | 5/2000 | Leonard et al. | |
| 6,186,962 | B1 * | 2/2001 | Lloyd et al. | 600/587 |
| 6,659,967 | B1 * | 12/2003 | Steinberg | 600/587 |
| 7,097,625 | B2 * | 8/2006 | Steinberg | 600/587 |
| 7,232,415 | B2 * | 6/2007 | Steinberg | 600/587 |
| 7,311,676 | B2 * | 12/2007 | Park | 600/587 |
| 7,530,975 | B2 * | 5/2009 | Hunter | 604/500 |
| 7,615,014 | B2 * | 11/2009 | Omata et al. | 600/587 |
| 7,648,470 | B2 * | 1/2010 | Omata | 600/591 |
| 7,780,612 | B2 * | 8/2010 | Ross | 602/5 |
| 2006/0064038 | A1 * | 3/2006 | Omata et al. | 600/587 |

FOREIGN PATENT DOCUMENTS

| | | |
|---|---|---|
| JP | 10-179524 | 7/1998 |
| JP | 2006-329935 | 12/2006 |
| JP | 2005-312745 | 11/2010 |
| WO | 2008-136140 A1 | 11/2008 |

OTHER PUBLICATIONS

Japanese Office Action for Application No. 2007-120861 dated Jan. 4, 2012.

* cited by examiner

MUSCLE HARDNESS METER

CROSS REFERENCE TO RELATED APPLICATIONS

The present application is a National Stage of International Application No. PCT/JP2007066360 filed on Aug. 23, 2007 and which claims priority to Japanese Patent Application No. 2007-120861 filed on May 1, 2001, the entire contents of which are being incorporated herein by reference.

BACKGROUND

The present invention relates to a muscle hardness meter which measures the hardness of muscle tissue of a living organism.

Heretofore, a range of muscle hardness meters have been used that measure the hardness of muscle tissue by applying pressure to a living organism.

These muscle hardness meters are provided with a primary pin that touches the living organism, and a secondary cylinder that encloses the primary pin (for example, refer to Patent document 1). The secondary cylinder is provided such that it can move forward or draw back with respect to the primary pin, and is continuously urged towards its distal side by a coiled spring. Furthermore, a switch is provided at a predetermined location at the rear of the secondary cylinder.

In such a construction, tension is applied to a section to be measured by pressing the front face of the secondary cylinder against the periphery of the section to be measured. In this state, the primary pin is pushed into the section to be measured. At this time, the secondary cylinder is installed such that it can move forward or draw back. Accordingly, the secondary cylinder sustains the pressure (reactive force) from the periphery of the section to be measured. As a result, the secondary cylinder resists the force exerted by the coiled spring, and regresses with respect to the primary pin. Then, the switch at its rear is turned on by the secondary cylinder at a certain timing, and a trigger signal is output from the switch. At this timing, the pressure (reactive force) that the primary pin sustains from the section to be measured is measured, so that the hardness of the muscle tissue of the living organism is measured.

[Patent document 1] Japanese Unexamined Patent Application, First Publication No. 10 H10-179524

However, in the muscle hardness meter as described above, the pressure value that the secondary cylinder sustains is set in advance according to the mechanical structure of the amount of shift (amount of regress) of the secondary cylinder and the spring constant of the coiled spring. Therefore, the dispersion of the pressure value set becomes large. As a result, there is a problem in that the hardness of muscle tissue cannot be measured accurately.

Furthermore, there is a case in which the pressures that the secondary cylinder and the primary pin sustain change rapidly due to the amount of force in the vicinity of the switch. In this case, the trigger signal cannot be output at appropriate timing. Therefore, there is a problem in that measurement cannot be performed with high accuracy.

Therefore, it is desirable to provide a muscle hardness meter that can make measurements easily with high accuracy using a simple construction.

SUMMARY

A muscle hardness meter according to an embodiment, which measures the hardness of muscle tissue of a living organism, includes: an auxiliary part which touches a periphery of a section of the living organism to be measured so as to apply pressure to the periphery; a touching part which touches the section to be measured so as to apply pressure to the section to be measured; a first pressure sensor which measures pressures that the touching part and the auxiliary part sustain, respectively, from the section to be measured and the periphery, and outputs a first measurement result; a second pressure sensor which measures a pressure that the touching part sustains from the section to be measured, and outputs a second measurement result; a notification part which notifies the second measurement result; and a control part which determines whether or not the first measurement result reaches a reference pressure value input in advance and notifies the second measurement result to the notification part at a time when it is determined that the first measurement result reaches the reference value.

In such a construction, the control part determines whether or not the measurement result of the first pressure sensor has reached the reference pressure value input in advance, and if it is determined to have reached the reference pressure value, notifies the measurement result of the second pressure sensor to the notification part at a time when the determination is made.

As a result, measurement can be performed easily with high accuracy using a simple construction.

Moreover, the above described muscle hardness meter may further include an input section which inputs the reference pressure value in advance, and the input section may include a plurality of pressure value selecting sections in which a plurality of pressure values determined in stages in advance are set, and the pressure value set in one of the plurality of pressure value selecting sections may be set as the reference pressure value.

In such a construction, it is possible to set the reference pressure value according to the section to be measured quickly and easily.

Furthermore, in the above-described muscle hardness meter, the plurality of pressure value selecting sections may be at least three.

As a result, it is possible to set the reference pressure value quickly and accurately using a simple construction.

Moreover, the above-described muscle hardness meter may further include a change section which changes the pressure values set for each of the plurality of pressure value selecting sections.

As a result, it is possible to increase the degree of freedom of setting the pressure values, so that it is possible to set the reference pressure value quickly and easily.

Furthermore, in the above-described muscle hardness meter, the change section may include a plurality of ratio selecting parts in which change ratios determined in stages in advance are set, and the pressure value that is changed according to the change ratio set by one which is selected from the plurality of ratio selecting parts may be set as the reference pressure value.

As a result, using a simple construction, it is possible to set a reference pressure value quickly and accurately.

Moreover, in the above-described muscle hardness meter, the control part may calculate an average value of a plurality of the second measurement results for a plurality of measurements.

As a result, it is possible to reduce the measurement error, enabling even more accurate measurement.

According to the present embodiment, the first pressure sensor measures the pressure that the touching part and the auxiliary part sustain. Depending on the measurement result, the control part instructs the notification part to notify the measurement result of the second pressure sensor. As a result, measurements can be made easily with high accuracy using a simple construction.

Additional features and advantages are described herein, and will be apparent from, the following Detailed Description and the figures.

DETAILED DESCRIPTION

Hereunder is a description of a muscle hardness meter according to an embodiment, with reference to the drawings.

Figure 1:
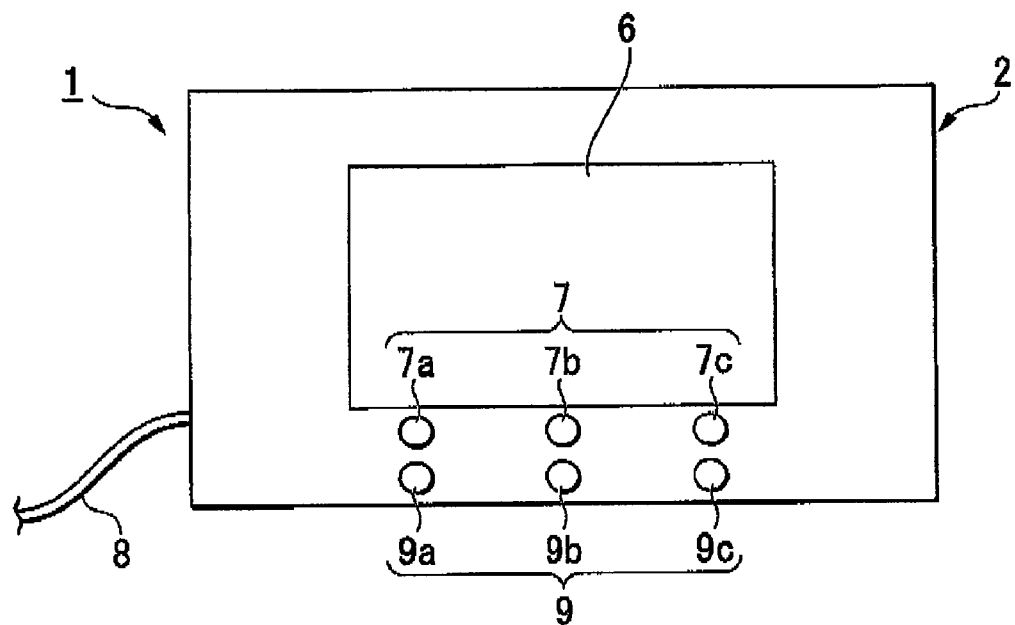
FIG. 1 is an overall structural diagram showing a muscle hardness meter 5 according to an embodiment.
Figure 1:
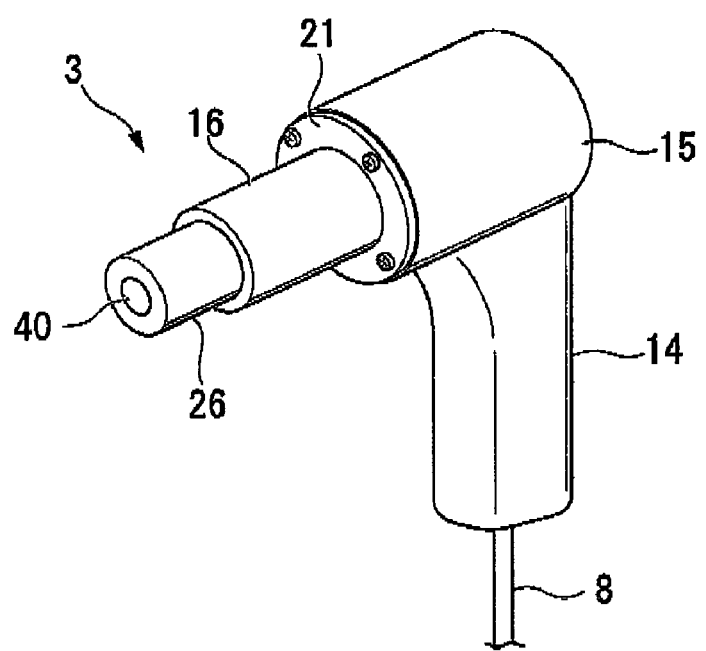

FIG. 1 shows a muscle hardness meter of an embodiment.

A muscle hardness meter 1 includes a device body part 2 having a rectangular shape, and a probe 3 which is connected to the device body part 2 via a cable 8.

A rectangular display part (notification part) 6 for displaying a range of information, is provided on the top panel of the device body part 2.

The display part 6 may be a liquid crystal display, for example.

A pressure value input section (input section) 7 and a change input section (change section) 9, which are described later, are provided on the top face of the device body part 2.

The probe 3 includes a holding part 14 for a user to hold. The holding part 14 has a long and narrow rectangular shape. A cylindrical probe body part 15 with a base is provided on the distal end thereof. The probe body part 15 is formed integrally with the holding part 14.

The axial direction of the probe body part 15 is a direction that intersects the longitudinal direction of the holding part 14.

A cylindrical support cylinder part (support part) 16 is provided at the open end of the probe body part 15. A proximal end flange 21 with the same diameter as the open end of the probe body part 15 is provided at the proximal end part of the support cylinder part 16. The proximal end flange 21 extends outward in the direction of the diameter of the support cylinder part 16. The proximal end flange 21 of the support cylinder part 16 is fixed to the probe body part 15 such that it covers the open end of the probe body part 15.

Figure 2:
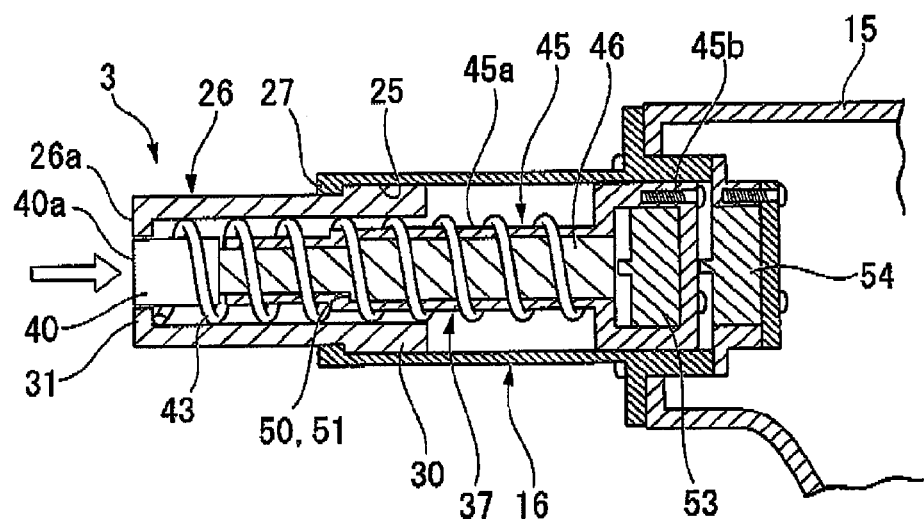
FIG. 2 is a cross-sectional diagram showing a side view of a part of a probe in the muscle hardness meter according to the embodiment of the present invention shown in FIG. 1.

A front flange 27 which is directed inwards in the direction of the diameter, is provided at the distal end of the support cylinder part 16 as shown in FIG. 2.

A cylindrical auxiliary cylinder part (auxiliary part) 26 is inserted into a cylinder cavity 25 of the support cylinder part 16.

A proximal end flange 30 is formed at the proximal end part of the auxiliary part 26. The outer diameter of the proximal end flange 30 is greater than the inner diameter of the front flange 27. Therefore, the proximal end flange 30 abuts the front flange 27. As a result, the auxiliary part 26 is prevented from detaching from the support cylinder part 16.

A front flange 31 is provided at the distal end of the auxiliary part 26.

A primary pin part 37 is provided inside the support cylinder part 16 and the auxiliary part 26. The axis of the primary pin part 37 is the same axis as that of the support cylinder part 16 and the auxiliary part 26. The dimension of the primary pin part 37 in the longitudinal direction is longer than the dimensions of both the support cylinder part 16 and the auxiliary part 26 in the longitudinal direction. Therefore, the distal end of the primary pin part 37 protrudes from the front flange 27 of the support cylinder part 16.

The primary pin part 37 is supported such that it can move in the axial direction in the support cylinder part 16. The primary pin part 37 includes a cylindrical outer wall part 45 with a base, and a cylindrical core part 46. The core part 46 passes through the inside of the outer wall part 45. The core part 46 is supported such that it can move backward and forward in the axial direction.

The outer wall part 45 includes a small diameter part 45a and a large diameter part 45b provided at the proximal end part of the small diameter part 45a. The small diameter part 45a and the large diameter part 45b are integrally formed. A step part 50 is formed on the inner peripheral surface of the small diameter part 45a.

Furthermore, a step part 51 is formed on the outer peripheral surface of the core part 46. The step parts 50 and 51 are abutted. Thus, the core part 46 is prevented from detaching from the front of the outer wall part 45.

At the tip of the core part 46, a female thread part, which is not illustrated, is 25 formed, which recedes from the front towards the rear A cylindrical front tip (touching part) 40 is provided at the front of the primary pin part 37. A male thread part, which is not illustrated, is provided on the rear surface of the front tip 40. The male thread part is screwed into the female thread part of the core part 46. In this manner, the front tip 40 is fitted such that it can be attached to or removed from the front of the primary pin part 37.

A second pressure sensor 53 made by a semiconductor, for example, is provided inside of the large diameter part 45b. When pressure is applied to the front tip 40, the core part 46 moves toward the rear with respect to the outer wall part 45. The second pressure sensor 53 measures the pressure of the core part 46 at this time.

A first pressure sensor 54 is provided behind the second pressure sensor 53, and outside of the base of the large wall part 45b. When pressure is applied to the auxiliary part 26 and the front tip 40, the primary pin part 37 moves toward the rear with respect to the support cylinder part 16. The first pressure sensor 54 measures the pressure of the primary pin part 37 at this time.

A coiled spring 43 is provided on the outer periphery of the primary pin part 37. That is, the primary pin part 37 passes through the inside of the coiled spring 43. The dimension of the coiled spring 43 in the longitudinal direction (dimension in the longitudinal direction in a state of no elastic deformation) is longer than the dimension of the small diameter part 45a in the longitudinal dimension. The inner diameter of the coiled spring 43 is larger than the outer diameter of the small diameter part 45a and the inner diameter of the front flange 31. The coiled spring 43 is located between the front face of the large diameter part 45b and the inner face of the front flange 31. As a result, the auxiliary part 26 is continuously urged toward the distal side. Therefore, the proximal end flange 30 abuts the front flange 27, so that the auxiliary part 26 is maintained in a state in which it protrudes from the front of the support cylinder part 16.

In an unloaded condition in which there is no external force applied, the front face 26a of the auxiliary part 26 is on the same plane as the front face 40a of the front tip 40.

Figure 3:
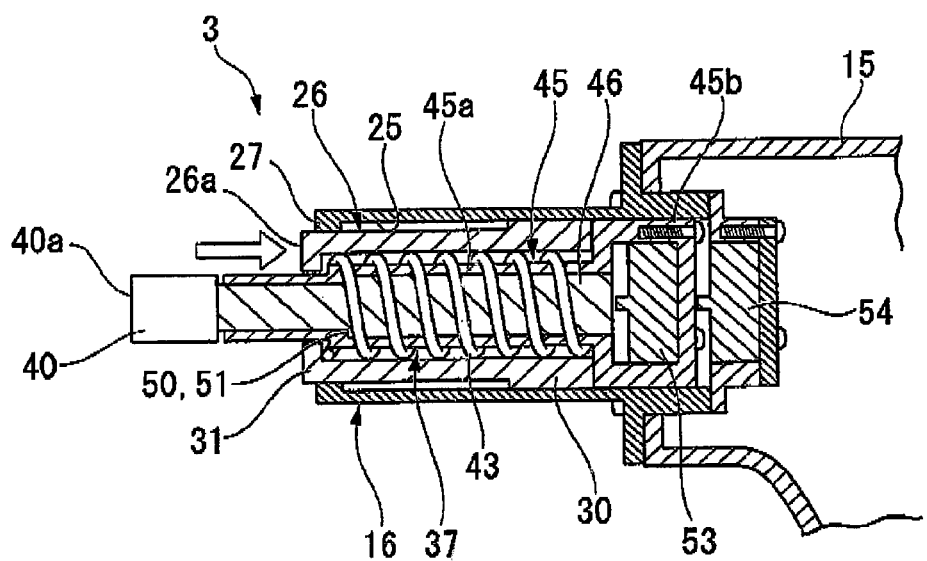
FIG. 3 is a cross-sectional diagram showing a state in which an auxiliary cylinder part of the probe of FIG. 2 is pushed into a support cylinder part.

If pressure is applied to the auxiliary part 26 toward its proximal end, the auxiliary part 26 resists the force exerted by the coiled spring 43 and moves in the direction whereby the coiled spring 43 contracts, as shown in FIG. 3.

Figure 4:
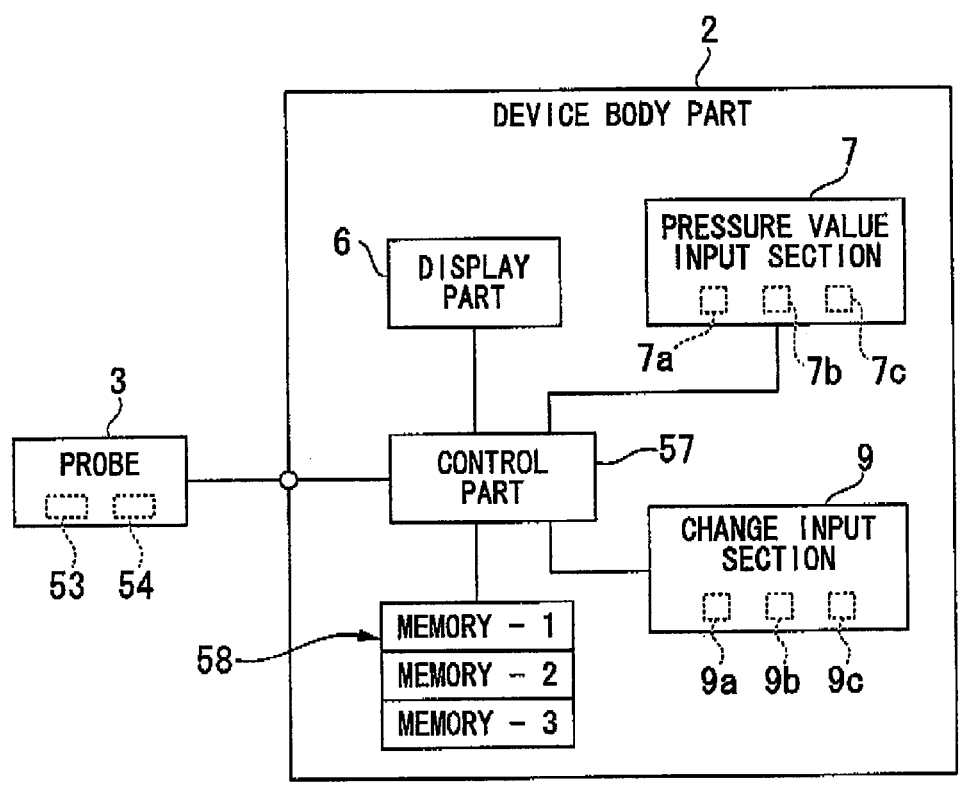
FIG. 4 is a block diagram showing each function of the muscle hardness meter according to the embodiment shown in FIG. 1.

As shown in FIG. 4, the device body part 2 includes a control part 57 which controls the overall device, A second pressure sensor 53 and a first pressure sensor 54 in the probe 3 are connected to the control part 57. Furthermore, a memory 58 which stores varies of information, a pressure value input section 7, and a change input section 9, are connected to the control part 57, A measuring person selects a button in each of the pressure value input section 7 and the change input section 9, and presses them. Pressure values (reference pressure values), which are references corresponding to the buttons pressed, are stored in the memory 58.

The pressure value input section 7 has a low pressure value button 7a, a mid pressure value button 7b, and a high pressure value button 70, in which the pressure values are determined in stages. Pressure values of 2 kg, 5 kg, and 10 kg are allocated to the low pressure value button 7a, the mid pressure value button 7b, and the high pressure value button 7c respectively, When any one of the low pressure value button 7a, the mid pressure value button 7b, or the high pressure value button 7c is pressed, the pressure value signal allocated to the button pressed is output to the control part 57. In this manner, the low pressure value button 7a, the mid pressure value button 7b, and the high pressure value button 7c function as a pressure value selecting section.

The change input section 9 changes the predetermined pressure value via the low pressure value button 7a, the mid pressure value button 7b, or the high pressure value button 7c, being pressed. The change input section 9 has a first ratio button 9a, a second ratio button 9b, and a third ratio button 9c, whose change ratios are determined in stages. The first ratio button 9a, the second ratio button 9b, and the third ratio button 9c are allocated ratios of 20%, 50%, and 75% respectively. When any one of the first ratio button 9a, the second ratio button 9b, or the third ratio button 9c is pressed, the change ratio signal allocated to the button pressed is output to the control part 57. In this manner, the first ratio button 9a, the second ratio button 9b, and the third ratio button 9c function as a ratio selecting section.

Next is a description of the operation of the muscle hardness meter 1 according to the present embodiment constructed in this way.

Here the description is made under the assumption that a reference pressure value, being an initial value, is stored in the memory 58 in advance.

Figure 5:
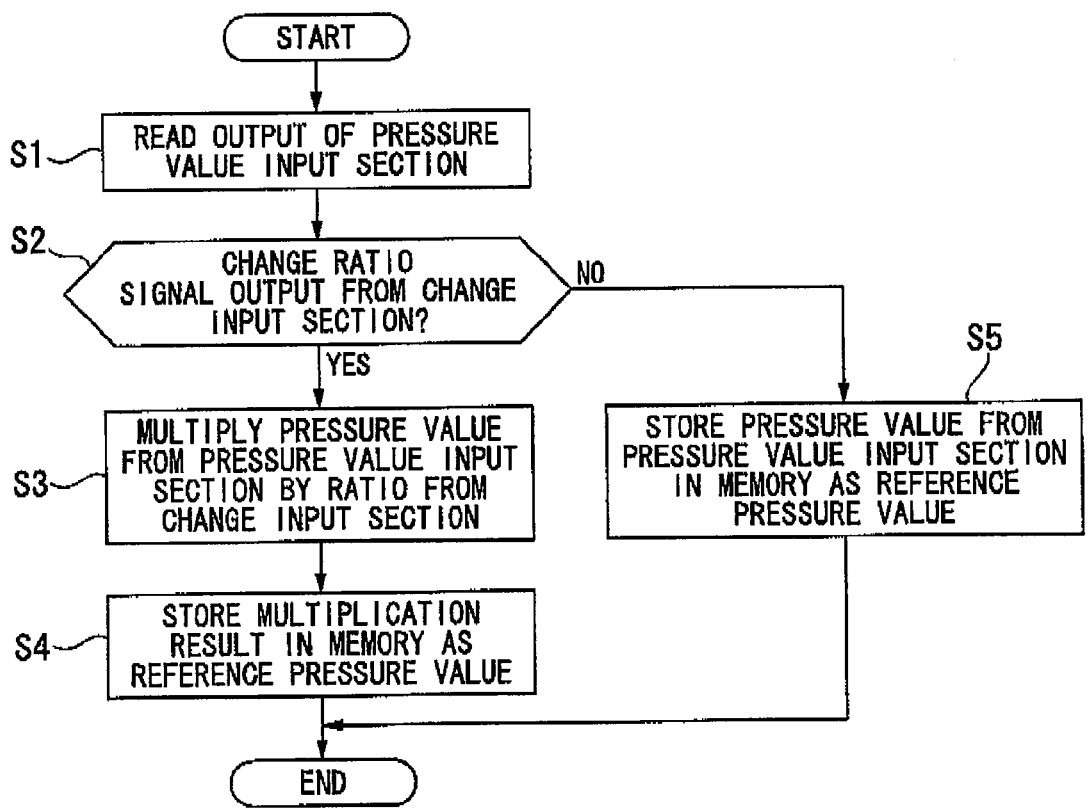
FIG. 5 is a flow chart showing the operation of a control part for storing a reference pressure value, of the muscle hardness meter according to the embodiment shown in FIG. 1.

FIG. 5 is a flow chart showing the operation of the control part 57 for storing the reference pressure value.

Firstly, the measuring person selects and switches on any one of the low pressure value button 7a, the mid pressure value button 7b, or the high pressure value button 7c. In the case where the section to be measured is soft, the low pressure value button 7a is selected, and in the case where it is hard, the high pressure value button 7c is selected. For example, suppose the low pressure value button 7a is selected and pressed. When the low pressure value button 7a is pressed, the pressure value signal is output to the control part 57. The control part 57 reads the pressure value signal from the low pressure value button 7a (step S1). Next, it reads the output of the change input section 9. The control part 57 determines whether or not a change ratio signal is output from the change input section 9 within a predetermined time (step S2).

In the case where the change input section 9 is not pressed, the control part 57 determines that a change ratio signal is not output from the change input section 9 in the predetermined time (determines No in step S2). In this case, it stores the pressure value signal from the low pressure value button 7a in the memory 58 as a reference pressure value (step S5). That is, lithe measuring person does not select and switch on the first ratio button 9a, the second ratio button 9b, or the third ratio button 90 within the predetermined time after switching on the low pressure value button 7a, the pressure value (2 kg) predetermined by the low pressure value button 7a is stored as the reference pressure value.

On the other hand, if the measuring person selects and switches on the first ratio button 9a, the second ratio button 9b, or the third ratio button 9c within the predetermined time after switching on the low pressure value button 7a, the pressure value (2 kg) predetermined by the low pressure value button 7a is changed corresponding to the predetermined ratio. The pressure value after the change, is stored as the reference pressure value. The case where the first ratio button 9a is selected and pressed will be described hereunder.

Next, in the case where the change input section 9 is pressed, the control part 57 determines that a change ratio signal is output from the change input section 9 within the predetermined time (determines Yes in step S2). In this case, the pressure value (2 kg) set in the low pressure value button 7a is multiplied by the ratio (20%) set in the first ratio button 9a (step S3). To be specific, it becomes 2 kg×0.2=0.4 kg. Next, the control part 57 stores the multiplied result (0.4 kg) in the memory 58 as the reference pressure value (step S4).

The above-described, flow is described under the assumption that the low pressure value button 7a and the first ratio button 9a are pressed. Alternatively, the reference pressure value may be calculated for combinations of the selection of the buttons 7a, 7b, or 7c, the selection of the buttons 9a, 9b, or 9; or the selection of no change input section pressed.

Figure 6:
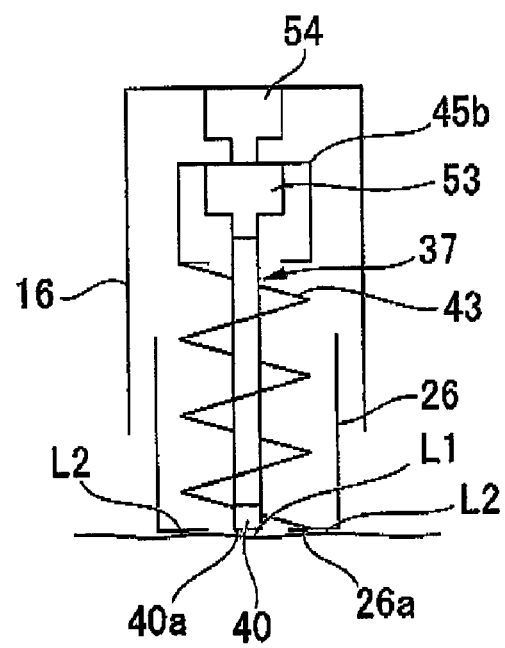
FIG. 6 is a diagram showing, schematically, an aspect of where the muscle hardness meter according to the embodiment shown in FIG. 1 measures a section to be measured.
Figure 7:
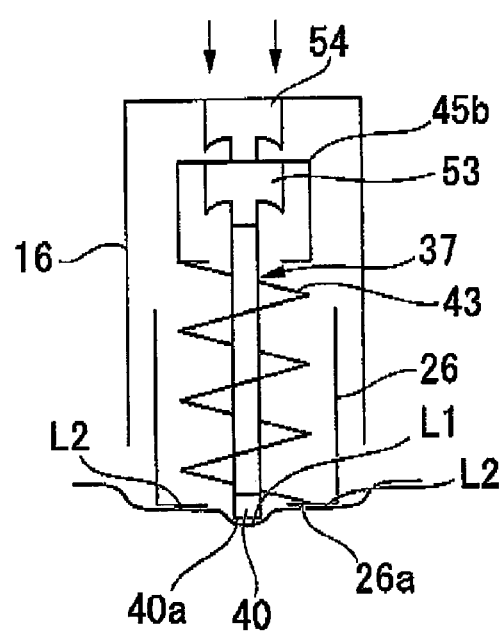
FIG. 7 is an explanatory diagram showing a state in which the auxiliary cylinder part of FIG. 6 is pushed into the support cylinder part.

FIG. 6 and FIG. 7 are explanatory diagrams showing, schematically, an aspect of the measurement by the probe 3. FIG. 6 and FIG. 7 are simplified in order to simplify the description. FIG. 6 is an explanatory diagram showing an aspect of where the front tip and the auxiliary cylinder part touch a section to be measured and its periphery.

As described above, the reference pressure value is stored in advance in the memory 58. Next, the measuring person holds the holding part 14, and the front face 40a of the front tip 40 touches a section to be measured LI. As a result, the front face 26a of the auxiliary part 26 also touches the peripheral part (vicinity) L2 of the section to be measured. In this state, by pressing the probe 3, pressure is applied to the section to be measured LI and the peripheral part L2. At this time, by pressure being applied to the peripheral part L2 by the auxiliary part 26, tension is applied to the section to be measured Li, so the flexure on the section to be measured L1 disappears. Moreover, by pressure being applied to the section to be measured L1 and the peripheral part L2, the front tip 40 and the auxiliary part 26 sustain pressure (reactive force) from the section to be measured L1 and the peripheral part L2. As a result, the auxiliary part 26 resists the force exerted by the coiled spring 43, and is pushed into. the support cylinder part 16. At this time, the pressure sustained from the peripheral part L2 is transmitted to the first pressure sensor 54 from the auxiliary part 26 via the coiled spring 43 and the large diameter part 45b. On the other hand, the pressure sustained from the section to be measured Li is transmitted to the second pressure sensor 53 from the front tip 40 via the primary pin part 37. Furthermore, the stress is transmitted to the first pressure sensor 54 from the second pressure sensor 53.

That is, the first pressure sensor 54 measures the pressure that the front tip 40 and the auxiliary part 26 sustain. On the other hand, the second pressure sensor 53 measures the pressure that only the front tip 40 sustains.

Measurement is performed as follows.

Figure 8:
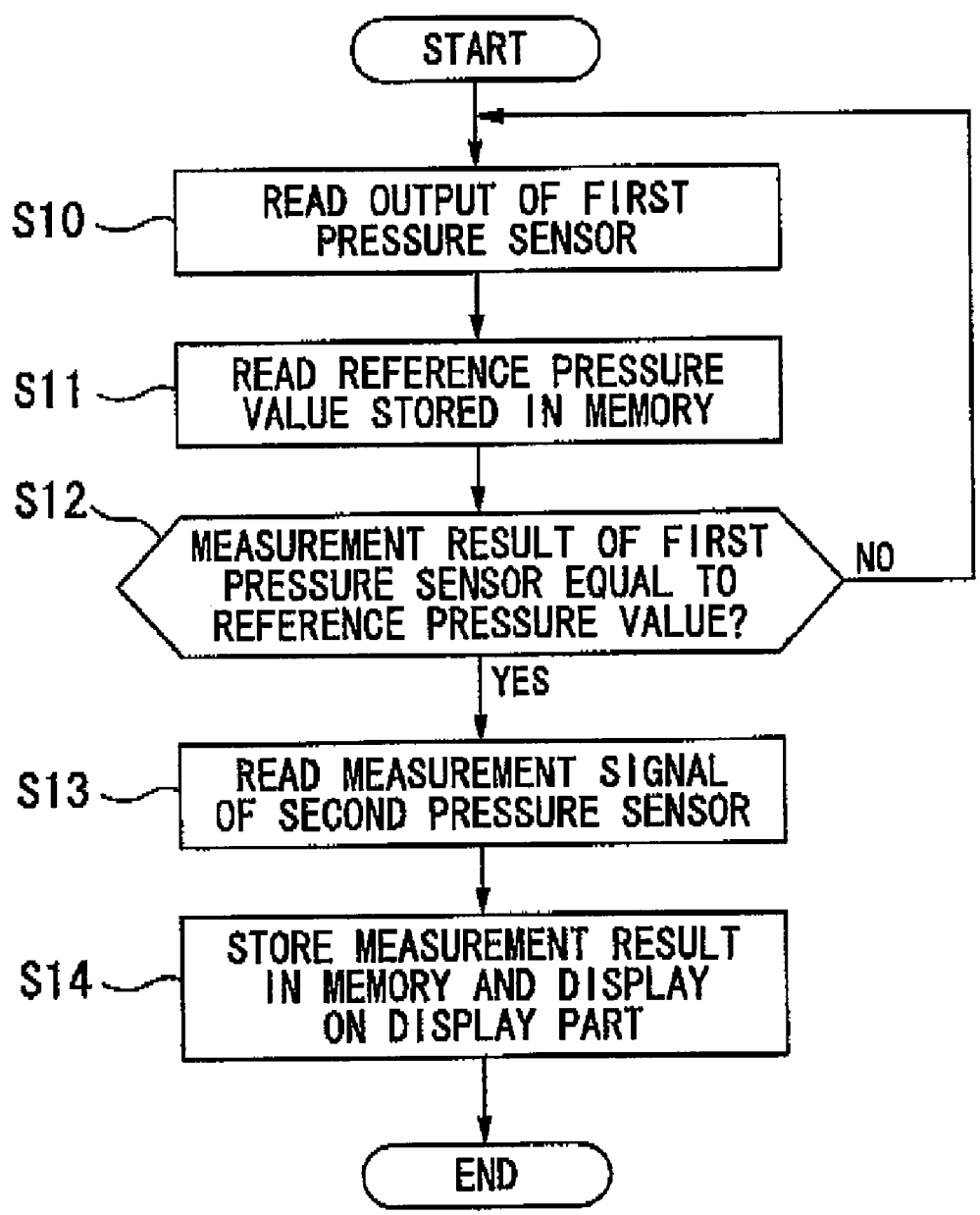
FIG. 8 is a flow chart showing the operation of the control part of the muscle hardness meter according to the embodiment shown in FIG. 1 at the time of measurement.

FIG. 8 is a flow chart showing the operation when the control part 57 performs a measurement.

Firstly, the control part 57 reads the output of the first pressure sensor 54 when pressure is applied to the probe 3. Then, it determines whether a measurement signal is output from the first pressure sensor 54 (step S10). If it determines that a measurement signal is output, it then reads the reference pressure value stored in the memory 58 (step S11). It then determines whether the measurement result of the first pressure sensor 54 and the reference pressure value are the same or not (step S12). If the control part 57 determines that the measurement result of the first pressure sensor 54 is less than (not the same as) the reference pressure value (determines No in step S12), the flow returns to step S10, and the process is repeated.

Furthermore, when the probe 3 is pushed in, the pressure that the front tip 40 and the auxiliary part 26 sustain increases gradually, and the pressure reaches the reference pressure value.

That is, when the pressure that the front tip 40 and the auxiliary part 26 sustain reaches the reference pressure value, the control part 57 determines that the measurement result of the first pressure sensor 54 is the same as the reference pressure value (determines Yes in step S12). Next, it reads the measurement signal from the second pressure sensor 53 (step S13). Then, the control part 57 stores the measurement result of the second pressure sensor 53 in the memory 58, and also displays the measurement result on the display part 6 (step S14). As a result, the hardness of the section to be measured L1 is notified to the measuring person.

As above, according to the muscle hardness meter 1 of the present embodiment, a reference pressure value is stored in advance in the memory 58. Then, the control part 57 displays the measurement result of the second pressure sensor 53 depending on the measurement result of the first pressure sensor 54 and the reference pressure value. Therefore, it is possible to reduce the dispersion of the reference pressure value that is set. Moreover, when the pressure that the front tip 40 and the auxiliary part 26 sustain reaches the reference pressure value, the measurement result of the second pressure sensor 53 can be read immediately. Accordingly, measurement can be performed easily and with high accuracy using a simple construction.

Since the pressure value input section 7 is provided, it is possible to set a reference pressure value according to the section to be measured quickly and easily.

The arrangement is such that setting can be done in three stages of the low pressure value button 7a, the mid pressure value button 7b, and the high pressure value button 70. Therefore, it is possible to set the reference pressure value quickly and accurately using a simple construction.

A change input section 9 is provided. Therefore, it is possible to increase the degree of freedom in the setting of the pressure value, and to set the reference pressure value quickly and easily.

The arrangement is such that setting can be done in three stages of the first ratio button 9a, the second ratio button 9b, and the third ratio button 9c, Therefore, it is possible to set a reference pressure value quickly and accurately using a simple construction.

Heretofore, reference pressure values have been set mechanically using a coiled spring, a switch, or the like. In these cases, when trying to change the reference pressure value according to the section to be measured, it becomes troublesome to make adjustments such as changing the coiled spring, changing the location of the switch, and the like.

According to the muscle hardness meter 1 of the present embodiment, it is possible to set the reference pressure value quickly and with high accuracy by only simple operations of the pressure value input section 7, the change input section 9, and the like.

In the above-described embodiment, one measurement of the second pressure sensor 53 is displayed on the display part 6 as the measurement result. However, this is not a limitation. For example, a plurality of measurements may be performed. The control part 57 reads the values of the plurality (for example three) of measurements of the second pressure sensor 53. The arrangement may be such that the average value of them is calculated, and the calculation result is displayed on the display part 6 as the measurement result As a result, it is possible to perform measurements accurately of a living organism in which dispersion in the measurement results is likely to be great.

In the embodiment, the measurement result of the second pressure sensor 53 is displayed on the display part 6 as it is. However, this is not a limitation. For example, the arrangement may be such that the measurement result of the second pressure sensor 53 is subtracted from the measurement result of the first pressure sensor 54, and the subtraction result based on the difference between the two is used as the measurement result. As a result, it is possible to reduce the dynamic range of the processing signals, so that the construction can be simplified.

In the embodiment, a low pressure value button 7a, a mid pressure value button 7b, and a high pressure value button 7c are provided. However, this is not a limitation. For example, two, four, or more selection buttons may be provided. Moreover, the arrangement may be such that the reference pressure value is set continuously variably, in the range of 0 to 10 kg for example, without providing the low pressure value button 7a, the mid pressure value button 7b, and the high pressure value button 7c.

The case is described in which both a pressure value input section 7 and a change input section 9 are provided, but it may be that only the pressure value input section 7 is provided. However, it is preferable that a change input section 9 is provided from the standpoint of setting the reference pressure value precisely.

The measurement result of the second pressure sensor 53 is notified via the display part 6. However, this is not a limitation, and appropriate modification is possible. For example, the value of the measurement result may be notified by an audible output.

The present invention can be used for a muscle hardness meter for measuring the hardness of muscle tissue of a living organism. According to the muscle hardness meter, it is possible to measure the hardness of muscle tissue of a living organism easily with high accuracy by using a simple construction.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A muscle hardness meter which measures hardness of muscle tissue of a living organism, the muscle hardness meter comprising:
   an auxiliary part which is configured to touch a periphery of a section of the living organism to be measured so as to apply pressure to the periphery;
   a touching part which is configured to touch the section to be measured so as to apply pressure to the section to be measured;
   a first pressure sensor which, measures both of a first pressure that the touching part sustains from the section to be measured and a second pressure that the auxiliary part sustains from the periphery, and outputs a total of the first pressure and the second pressure as a first measurement result;
   a second pressure sensor which measures the first pressure that the touching part sustains from the section to be measured, and outputs the first pressure as a second measurement result;
   a notification part which notifies the second measurement result; and
   a control part which determines whether or not the first measurement result reaches a reference pressure value input in advance and notifies the second measurement result to the notification part at a time when it is determined that the first measurement result reaches the reference value.

2. A muscle hardness meter according to claim 1, further comprising: an input section which inputs the reference pressure value in advance, wherein the input section includes a plurality of pressure value selecting sections in which a plurality of pressure values determined in stages in advance are set, wherein the pressure value set in one of the plurality of pressure value selecting sections is set as the reference pressure value.

3. A muscle hardness meter according to claim 2, wherein the plurality of pressure value selecting sections are at least three.

4. A muscle hardness meter according to claim 2, further comprising a change section which changes the pressure values set for each of the plurality of pressure value selecting sections.

5. A muscle hardness meter according to claim 4, wherein the change section includes a plurality of ratio selecting parts in which change ratios determined in stages in advance are set, wherein the pressure value that is changed according to the change ratio set by one which is selected from the plurality of ratio selecting parts is set as the reference pressure value.

6. A muscle hardness meter according to claim 1, wherein the control part calculates an average value of a plurality of the second measurement results for a plurality of measurements.

* * * * *